United States Patent [19]
Abe et al.

[11] Patent Number: 5,587,453
[45] Date of Patent: Dec. 24, 1996

[54] PROCESS FOR PURIFYING METHACRYLATE

[75] Inventors: Takafumi Abe; Mitsuhiro Nishikawa; Susumu Naitoh, all of Niigata, Japan

[73] Assignee: Mitsubishi Gas Chemical Company, Inc., Tokyo, Japan

[21] Appl. No.: 381,740

[22] Filed: Feb. 1, 1995

[30]  Foreign Application Priority Data

Feb. 25, 1994 [JP] Japan .................................... 6-028191
Mar. 25, 1994 [JP] Japan .................................... 6-055788
Mar. 25, 1994 [JP] Japan .................................... 6-055789
Apr. 7, 1994 [JP] Japan .................................... 6-069416

[51] Int. Cl.$^6$ .................................................... C08F 6/24
[52] U.S. Cl. ............................................ 528/488; 528/492
[58] Field of Search ..................................... 528/488, 492

[56]   References Cited

U.S. PATENT DOCUMENTS 5,243,063   9/1993   Devicaris et al. ...................... 558/304

FOREIGN PATENT DOCUMENTS 0266906   5/1988   European Pat. Off. .

*Primary Examiner*—Thomas R. Weber
*Attorney, Agent, or Firm*—Frishauf, Holtz, Goodman, Langer & Chick, P.C.

[57]   ABSTRACT

A process for purifying a methacrylate which comprises contacting the methacrylate with an oximating agent, such as hydroxylamine hydrochloride or an aqueous alkali solution, such as an aqueous sodium hydroxide solution, or both, and then separating and collecting the resultant purified methacrylate. The process serves to remove compounds which discolor the methacrylate, to obtain a high-quality methacrylate.

20 Claims, No Drawings

PROCESS FOR PURIFYING METHACRYLATE

BACKGROUND OF THE INVENTION

1. Field of the Invention

The present invention relates to a process for purifying a methacrylate which can efficiently, economically and advantageously remove coloring substances, particularly impurities such as biacetyl from the methacrylate.

The methacrylates have been widely used as optical materials for organic glasses, optical fibers, various coating materials, contact lens materials and the like.

2. Description of the Related Art

As industrial techniques for manufacturing methyl methacrylate, there are known an acetone cyanohydrin method (an ACH method) which involves the production of ammonium sulfate as a by-product, an improved ACH method which does not involve the production of ammonium sulfate, a $C_4$ oxidation method and the like.

Methacrylic acid or methyl methacrylate obtained by any of these methods can be subjected to an esterification reaction with an alcohol or an ester exchange reaction to prepare a desired methacrylate.

The methacrylate obtained by this method contains coloring substances in such an amount as not to be negligible, which coloring substances are formed when the methacrylate is exposed to a strong oxidizing agent and a high temperature in steps of its preparation.

The presence of the coloring substances has a large influence on the commercial value of the methacrylate, depending upon its use. Particularly in the case that the methacrylate is used for an optical fiber or the like, there occurs a serious problem that the presence of the coloring substances impairs the transmittance of light having a specific wavelength.

As techniques for removing the coloring substances from the methacrylate, some methods are known. For example, they are a method which comprises separating the coloring substances by distillation at a high reflux ratio in a high multi-stage tower, a method which comprises an adsorption treatment by the use of active carbon, a method which comprises passing the methacrylate on a solid adsorbent such as alumina (Japanese Patent Publication No. 18964/1985), and a method which comprises treating the methacrylate with an aromatic diamine or the like (EP 206,230).

The present inventors have investigated these known methods for removing the coloring substances from various angles. For example, when the above-mentioned method using the distillation is used in order to completely remove biacetyl having a low specific volatility which is the coloring substance from methyl methacrylate, there is a problem that enormous energy is required.

In sufficiently removing the coloring substances by the use of the active carbon, a huge amount of the active carbon is necessary owing to an adsorption/desorption equilibrium, and there is a problem that a considerable cost for the recovery of the used active carbon is additionally necessary.

The method which comprises passing the methacrylate on alumina also has a drawback that a huge amount of alumina is disadvantageously required for the treatment of the coloring substances.

In addition, in the method utilizing an aromatic diamine, a large excess of the reagent is required for the treatment of the coloring substances, and so this method is not considered to be practical.

SUMMARY OF THE INVENTION

An object of the present invention is to provide a process for easily obtaining a high-quality methacrylate which is scarcely colored.

Another object of the present invention is to provide a process for advantageously preparing a high-quality methacrylate on an industrial scale.

The present inventors have paid much attention to a fact that most of coloring substances with which a methacrylate is colored are compounds each having a carbonyl group, particularly diketones, and unsaturated ketones having a quinone structure in which a conjugated double bond is present. Thus, it has been found that these compounds each having the carbonyl group selectively react with hydroxylamine to form oximes, and on the other hand, hydroxylamine does not form any oxime with the carboxyl group of the methacrylate. In addition to this fact, it has also been found that the coloring substances can be easily removed from the methacrylate phase by reacting these compounds each having the carbonyl group with an aqueous solution of an alkali metal compound to form water-soluble compounds. The present invention has been completed on the basis of these knowledges.

According to the present invention, there is provided a process for purifying a methacrylate which comprises the steps of treating the methacrylate colored by coloring substances each having a carbonyl group with either or both of (a) an oximating agent capable of oximating the coloring substances each having the carbonyl group and (b) an aqueous alkali solution, and then separating and collecting the methacrylate from the thus treated solution. In short, the process of the present invention is characterized by treating a colored methacrylate with at least one treating agent selected from (a) an oximating agent and (b) an aqueous alkali solution.

DESCRIPTION OF PREFERRED EMBODIMENTS

A process of the present invention is, as described above, characterized by treating a colored methacrylate with (a) an oximating agent and/or (b) an aqueous alkali solution. This process includes the following preferable embodiments (1) to (5).

(1) A process which comprises the steps of treating the colored methacrylate with the oximating agent, and then separating and collecting the methacrylate from the thus treated solution (Process 1).

(2) A process which comprises the steps of treating the colored methacrylate with an aqueous alkali solution, particularly an aqueous solution of an alkali metal compound, and then separating and collecting the methacrylate from the thus treated solution (Process 2).

(3) A process which comprises the steps of treating the colored methacrylate with the aqueous alkali solution, further treating the same with the oximating agent, and then separating and collecting the methacrylate from the thus treated solution (Process 3).

(4) A process which comprises the steps of treating the colored methacrylate with a reducing agent or a sulfite, further treating the same with the oximating agent, and then separating and collecting the methacrylate from the thus treated solution (Process 4).

(5) A process which comprises the steps of treating the colored methacrylate with the aqueous alkali solution, further treating the same with the reducing agent or the sulfite, and then separating and collecting the methacrylate from the thus treated solution (Process 5).

The process of the present invention is directed to a process for purifying a methacrylate colored with trace amounts of coloring substances, whereby the trace amounts of the coloring substances alone are chemically converted, substantially without losing the methacrylate, into substances having largely different physical properties which can easily be separated by a usual distillation operation, thereby obtaining the substantially coloring substances-free methacrylate. Particularly in the case of using the oximating agent, diketones and unsaturated ketones having a conjugated double bond which are the coloring substances can be oximated or dioximated to be converted into high-boiling compounds, whereby they can easily be separated. In the case that the aqueous alkali solution is used, the coloring substances alone are reacted with the alkali to be easily converted into separable removable water-soluble compounds, thereby obtaining the substantially coloring substances-free methacrylate.

As the oximating agent which can be used in the process of the present invention, any agent can be used, so long as it can oximate the coloring substances each having a carbonyl group. From the viewpoints of easy availability and easy handling, salts of hydroxylamine and mineral acids are preferable, and above all, hydroxylamine hydrochloride and hydroxylamine sulfate are particularly preferable.

The amount of the salt of hydroxylamine and mineral acid is preferably in the range of 0.2 to 50 mols per mol of the coloring substances each having the carbonyl group. If the amount of the salt of hydroxylamine and mineral acid is less than the above-mentioned range, a desired purification effect cannot be obtained sometimes, and if it is more than the above-mentioned range, a manufacturing cost increases in vain and a disadvantage such as polymerization might occur.

As the aqueous alkali solution which can be used in the present invention, aqueous solutions of alkali metal compounds are particularly preferable. These alkali metal compounds can suitably be used in conformations such as hydroxides, oxides, carbonates and silicates. Above all, alkali hydroxides are most recommendable by which an excellent purification effect can be obtained and which are excellent in handling, safety, availability and economy, and among the alkali hydroxides, sodium hydroxide and potassium hydroxide are particularly preferable.

The amount of the alkali to be used in the present invention is preferably in the range of 0.1 to 50 mols, more preferably 1.0 to 20 mols in terms of an alkali metal per mol of the coloring substances each having the carbonyl group. If the amount of the alkali is less than this range, the purification effect is not always sufficient, and if it is more than the above-mentioned range, the manufacturing cost increases in vain and a disadvantage such as polymerization might occur.

The temperature of the treatment with the aqueous alkali solution in the process of the present invention is usually in the range of 0° to 100° C., preferably from ordinary temperature to 50° C. If the temperature is lower than this range, the purification effect is poor sometimes, and if it is more than the above-mentioned range, a side reaction such as polymerization might be brought about.

In the process of the present invention, either of the treatment with the oximating agent and the other treatment with the aqueous alkali solution is carried out for the colored methacrylate, but both of the treatments can also be done. In the case that both the treatment with the oximating agent and the treatment with the aqueous alkali solution are carried out, it is preferred to do the treatment with the aqueous alkali solution prior to the treatment with the oximating agent.

In the process of the present invention, another treatment with a reducing agent or a sulfite may be carried out together with the treatment with the oximating agent or the treatment with the aqueous alkali solution. In this case, no particular restriction is put on the order of these treatments, but the treatment with the reducing agent or the sulfite is preferably done after the treatment with the aqueous alkali solution or prior to the treatment with the oximating agent.

In a certain case, the methacrylate in which a coloring state is improved to some extent can be obtained even only by the treatment with the reducing agent or the sulfite without doing the treatment with the oximating agent or the aqueous alkali solution.

As the reducing agent which can be used herein, various kinds of metal hydrogen complex compounds are suitably used, but sodium borohydride is particularly preferable from the viewpoints of safety, easy handling, easy availability and economy. This reducing agent can suitably be used in the form of an aqueous alkali solution, a powder or tablets. No particular restriction is put on the amount of the reducing agent to be used, but this amount is preferably in the range of 0.1 to 50 mols, more preferably 0.5 to 5 mols per mol of the coloring substances each having the carbonyl group. The temperature of the treatment with the reducing agent is usually in the range of 0° to 100° C., preferably from ordinary temperature to 50° C.

Examples of the usable sulfite include various kinds of sulfites and hydrogensulfites, but sodium sulfite and sodium hydrogensulfite are most preferable from the viewpoints of safety, easy handling, easy availability and economy. No particular restriction is put on the amount of the sulfite to be used, but this amount is preferably in the range of 0.5 to 50 mols, more preferably 1.0 to 5 mols per mol of the coloring substances each having the carbonyl group. In addition, the temperature of the treatment with the sulfite is usually in the range of 0° to 100° C., preferably from ordinary temperature to 50° C.

No particular restriction is put on the preparation method of making the methacrylates, typically, methyl methacrylate, ethyl methacrylate, propyl methacrylate or butyl methacrylate can be applied to the process of the present invention, and the methacrylates contain coloring substances each having a carbonyl group such as biacetyl.

According to the process of the present invention, the coloring substances can be converted into such substances as to be easily separable by phase separation or distillation, whereby the coloring substances can be effectively removed. In consequence, the high-quality methacrylate can easily be obtained. Thus, it is apparent that the process of the present invention has an extremely large industrial merit.

Next, the present invention will be described in more detail with reference to examples and comparative examples, but the scope of the present invention should not be limited to these examples.

EXAMPLE 1

In a flask equipped with a reflux condenser and a stirrer were placed 50 g of methyl methacrylate containing 0.1% by weight of biacetyl and 50 g of methanol. This solution was colored light yellow, and its APHA value representing a color index was 100. Next, 5.5 g of a 1% by weight aqueous hydroxylamine hydrochloride solution was added to the solution, followed by stirring at room temperature for 2 hours.

The thus treated solution was analyzed by gas chromatography (GC), and as a result, any biacetyl was not detected.

This treated solution was further washed with water to remove methanol therefrom, and the resultant organic phase was distilled by a distilling apparatus equipped with a vigoureux fractionating column having an inner diameter of 15 mm and a height of 300 mm. The thus obtained methyl methacrylate fraction was colorless and transparent, and its APHA value was 5 or less.

EXAMPLE 2

The same procedure as in Example 1 was carried out except that 5.5 g of a 1% by weight aqueous hydroxylamine hydrochloride solution was replaced with 6.5 g of a 1% by weight aqueous hydroxylamine sulfate solution.

As a result, any biacetyl was not detected in a treated solution, and the APHA value of the resultant methyl methacrylate fraction was 5 or less.

EXAMPLE 3

The same procedure as in Example 1 was carried out except that methyl methacrylate was replaced with butyl methacrylate.

As a result, any biacetyl was not detected in a treated solution, and the APHA value of the resultant butyl methacrylate fraction was 5 or less.

Comparative Example 1

The same procedure as in Example 1 was carried out except a treatment with an aqueous hydroxylamine hydrochloride solution was not done.

As a result of analysis by GC, 0.05% by weight of biacetyl was detected in a treated solution, and the APHA value of the resultant methyl methacrylate fraction was 70.

EXAMPLE 4

In a flask equipped with a reflux condenser and a stirrer were placed 100 g of methyl methacrylate containing 0.2% by weight of biacetyl. This solution was colored yellow, and an APHA value representing a color index in comparison with a standard solution was 500 or more. Next, 50 g of a 1.4% by weight aqueous sodium hydroxide solution was added to the solution, followed by stirring at room temperature for 10 minutes. The thus treated solution was divided into a methyl methacrylate phase and an aqueous phase, and the methyl methacrylate phase was then analyzed by GC. As a result, the content of biacetyl decreased to 0.011% by weight. The APHA value of the methyl methacrylate phase obtained herein was 10, but when this phase was distilled, the APHA value of the resultant methyl methacrylate was 5 or less which was a value enough to denote high quality.

EXAMPLE 5

The same procedure as in Example 4 was carried out except that 50 g of a 1.4% by weight aqueous sodium hydroxide solution was replaced with 50 g of a 2.0% by weight aqueous potassium hydroxide solution.

As a result, the content of biacetyl in a methyl methacrylate phase was 0.010% by weight. When this phase was distilled, the APHA value of the resultant methyl methacrylate was 5 or less which was a value enough to denote high quality.

EXAMPLE 6

The same procedure as in Example 4 was carried out except that methyl methacrylate was replaced with butyl methacrylate. As a result, the content of biacetyl in a butyl methacrylate phase was 0.015% by weight. When this phase was distilled, the APHA value of the resultant methyl methacrylate was 5 or less which was a value enough to denote high quality.

Comparative Example 2

The same procedure as in Example 4 was carried out except that water alone was added in place of an aqueous sodium hydroxide solution. As a result, 0.18% by weight of biacetyl remained in a methyl methacrylate phase, and its APHA was 500 or more. Therefore, a purification effect was judged to be scarcely present.

EXAMPLE 7

In a flask equipped with a reflux condenser and a stirrer were placed 100 g of methyl methacrylate containing 0.2% by weight of biacetyl. This solution was colored yellow, and its APHA value representing a color number was 500 or more. Next, 50 g of a 1.4% by weight aqueous sodium hydroxide solution was added to the solution, followed by stirring at room temperature for 10 minutes.

The thus treated solution was divided into a methyl methacrylate phase and an aqueous phase, and the methyl methacrylate phase was then analyzed by GC. As a result, the content of biacetyl was 0.011% by weight, and its APHA value was 10 or less. Subsequently to the above-mentioned operation, the obtained methyl methacrylate phase was washed with 100 g of pure water, and 2.0 g of a 1% by weight aqueous hydroxylamine hydrochloride solution and 50 g of methanol were then added thereto, followed by stirring at room temperature for 2 hours. The thus treated solution was analyzed by GC, and as a result, any biacetyl was not detected.

This treated solution was further washed with water and then distilled in the same manner as in Example 1. The resultant methyl methacrylate fraction was colorless and transparent, and its APHA value was 5 or less.

What is claimed is:

1. A process for purifying a methacrylate which comprises contacting the methacrylate with at least one treating agent selected from the group consisting of (a) an oximating agent comprising at least one compound selected from the group consisting of hydroxylamine and a mineral acid salt thereof and (b) an aqueous alkali solution, and then separating and collecting the resultant purified methacrylate.

2. The process according to claim 1 wherein the treating agent is the oximating agent.

3. The process according to claim 1 wherein the treating agent is the aqueous alkali solution.

4. The process according to claim 1 wherein the methacrylate is first contacted with (b) the aqueous alkali solution, and then contacted with (a) the oximating agent.

5. The process according to claim 1 wherein (b) the aqueous alkali solution is an aqueous solution of an alkali metal compound.

6. The process according to claim 6 wherein the alkali metal compound is selected from the group consisting of sodium hydroxide and potassium hydroxide.

7. The process according to claim 1 which further comprises contacting the methacrylate with a reducing agent or a sulfite prior to the contacting with the oximating agent.

8. The process according to claim 1 which further comprises contacting the methacrylate with a reducing agent or a sulfite after the contacting with the aqueous alkali solution.

9. The process according to claim 1 wherein said treating agent is selected from the group consisting of hydroxylamine hydrochloride and hydroxylamine sulfate.

10. The process according to claim 1 wherein the methacrylate to be purified is discolored by an unsaturated ketone having a quinone structure in which a conjugated double bond is present.

11. The process according to claim 1 wherein the methacrylate to be purified is discolored by a diketone.

12. The process according to claim 11 wherein the diketone is biacetyl.

13. The process according to claim 11 wherein the treating agent is the aqueous alkali solution which is an aqueous alkali solution of an alkali metal compound selected from the group consisting of sodium hydroxide and potassium hydroxide and the alkali metal compound is in an amount of 0.1 to 50 moles per mol of the ketone.

14. The process according to claim 13 wherein the alkali metal compound is in an amount of 1.0 to 20 mols per mol of the ketone.

15. The process according to claim 14 wherein the contacting with the aqueous alkali solution is carried out at a temperature of 0° to 100° C.

16. The process according to claim 10 wherein the treating agent is the mineral acid salt of a hydroxylamine and is in an amount of 0.2 to 50 mols per mol of the ketone.

17. The process according to claim 7 wherein the contacting with the reducing agent or the sulfite is carried out at a temperature of 0° to 100° C.; the reducing agent is sodium borohydride in an amount of 0.1 to 5 mols per mole of the ketone; the sulfite is selected from the group consisting of sodium sulfite and sodium hydrogensulfite and the sulfite is in an amount of 0.5 to 50 mols per mol of the ketone.

18. The process according to claim 8 wherein the contacting with the reducing agent or the sulfite is carried out at a temperature of 0° to 100° C.; the reducing agent is sodium borohydride in an amount of 0.1 to 5 mols per mole of the ketone; the sulfite is selected from the group consisting of sodium sulfite and sodium hydrogensulfite and the sulfite is in an amount of 0.5 to 50 mols per mol of the ketone.

19. The process according to claim 1 wherein the methacrylate is selected from the group consisting of methyl methacrylate, ethyl methacrylate and butyl methacrylate.

20. The process according to claim 1 wherein the oximating agent is a salt of hydroxylamine and a mineral acid.

\* \* \* \* \*